US006183483B1

United States Patent
Chang

(10) Patent No.: US 6,183,483 B1
(45) Date of Patent: Feb. 6, 2001

(54) PEELING APPARATUS FOR REMOVING SURFACE PORTIONS OF HUMAN TISSUE WITH PURGING ARRANGEMENT

(76) Inventor: Henry Ping Chang, 2690 E. California Blvd., San Marino, CA (US) 91108

(*) Notice: Under 35 U.S.C. 154(b), the term of this patent shall be extended for 0 days.

(21) Appl. No.: 09/541,652

(22) Filed: Apr. 3, 2000

(51) Int. Cl.⁷ ................................................ A61B 17/50
(52) U.S. Cl. ......................................................... 606/131
(58) Field of Search .................................. 606/131, 132, 606/133; 433/88, 92

(56) References Cited

U.S. PATENT DOCUMENTS

| 4,492,575 | * | 1/1985 | Mabille | 433/88 |
| 5,037,431 | * | 8/1991 | Summers et al. | 606/131 |
| 5,100,412 | * | 3/1992 | Rosso | 606/131 |
| 5,810,842 | * | 9/1998 | Di Fiore et al. | 606/131 |
| 6,106,288 | * | 8/2000 | Brassil et al. | 433/88 |

* cited by examiner

Primary Examiner—Gene Mancene
Assistant Examiner—Eduardo C. Robert
(74) Attorney, Agent, or Firm—Raymond Y. Chan; David and Raymond

(57) ABSTRACT

A peeling apparatus for removing surface portions of human tissue by superficial abrasion caused by a stream of a mixture of air with at least one granular abrasive substance striking on the surface portion of the human tissue to be removed, wherein the peeling apparatus includes a purging arrangement includes a first and a second switch. The first switch includes a control switch valve connected at the first air dust, for regulating the compressed air flowing from the air filtering outlet member of the collection reservoir to the suction pump normally, and being selectively switched to cut off the connection between collection reservoir and the air inlet of the suction pump while instantaneously connecting the air outlet of the suction pump to the air filtering outlet member instead, so as to deliver the air output from the air outlet of the suction pump reversely to the air filtering outlet member for purging a clogged condition thereof The second switch is adapted for normally ensuring the air outlet of the suction pump connected to outside and selectively switching to instantaneously connect the air outlet of the suction pump to the fresh substance outlet member of the abrasive substance supply so as to deliver the air output from the air outlet of the suction pump reversely to the fresh substance outlet member for purging a clogged condition thereof.

12 Claims, 3 Drawing Sheets

PEELING APPARATUS FOR REMOVING SURFACE PORTIONS OF HUMAN TISSUE WITH PURGING ARRANGEMENT

FIELD OF THE PRESENT INVENTION

The present invention relates to peeling apparatus for controlled removal of surface portions of human tissue, and more particularly to a purging arrangement incorporated with the peeling apparatus, which is adapted to instantaneously purge the clogged air circuit safely in low cost without complicating the system structure.

BACKGROUND OF THE PRESENT INVENTION

In order to remove the metabolic dead tissue on skin surface for skin care and restoration purposes, a peeling apparatus is commonly used to effect a controlled application of reducing substances onto human tissue, for example the skin, for the purpose of obtaining a superficial abrasion of adjustable magnitude. For example, this abrasion could be of minimum value, known in general as "pealing" and consisting essentially in a removal of the outermost layers of the epidermis, or else of maximum value and consisting in a deep abrasion which could also involve the dermis.

The conventional peeling apparatus generally comprises a compressor conveniently generating compressed air, an abrasive or reducing substance supply means, supplying, for example, microcrystals of quartz, metal, dust or derivatives of aluminum, such as corundum, possibly having different grain size diameters, a suction means which is generally constituted by a suction pump and a collection reservoir connected to it, and a tool constituting the instrument manipulated by the medical operator to remove the portions of tissue.

The compressor maintains under pressure air contained within a reservoir, a pressure regulator connected in series with an output from the reservoir, and a solenoid valve which allows the air under pressure to flow out along a duct. The suction means comprises a reservoir connected to the duct by means of a flow regulator and a solenoid valve.

However, moisture and crystal quality can produce a clog that will quickly shut down the entire apparatus. In other words, the microcrystals may clog the outlets of the supply reservoir and used crystal reservoir, wherein when either the outlet of the supply reservoir which is connected to the tool or the outlet of the used crystal reservoir which is connected to the compressor is clogged, the air circuit of the peeling apparatus is broken and the ejection of crystal will be shut down too.

SUMMARY OF THE PRESENT INVENTION

The main object of the present invention is to provide a peeling apparatus for removing surface portions of human tissue comprising a purging arrangement adapted to instantaneously purge the clogged air circuit safely in low cost without complicating the system structure.

Another object of the present invention is to provide a purging arrangement adapted to be equipped in a peeling apparatus, which is easy to operate and which does not require for its construction the use of complicate components.

Another object of the present invention is to provide a purging arrangement adapted to be equipped in a peeling apparatus, which substantially increases the performance of the peeling apparatus by removing the clogged condition easily and rapidly.

Accordingly, in order to accomplish the above objects, the present invention provides a peeling apparatus for removing surface portions of human tissue by superficial abrasion caused by a stream of a mixture of air with at least one granular abrasive substance striking on the surface portion of the human tissue to be removed, wherein the peeling apparatus comprises:

an abrasive substance supply means supplying granular abrasive substances, such as microcrystals of quartz, metal, dust, or derivatives of aluminum, which comprises a supply reservoir storing a predetermined amount of fresh abrasive substance therein, and a fresh substance outlet member extended into the supply reservoir;

a peeling tool, which is an instrument adapted to be manipulated by a medical operator to remove the surface portions of the human tissue, having an input opening, a delivery hole and an output opening, wherein the input opening is connected to the fresh substance outlet member of the supply reservoir;

a suction means for providing a negative air pressure environment within the supply reservoir so as to cause a stream of a mixture of air and the granular abrasive substance traveling from the fresh substance outlet member to the peeling tool through the input opening thereof, wherein the suction means comprises a collection reservoir having a used substance inlet member connected to the output opening of the peeling tool and an air filtering outlet member, and a suction pump having an air outlet and an air inlet connecting with the air filtering outlet member of the collection reservoir through a first air duct, wherein by keeping in contact the delivery hole with the surface portion of the human tissue to be subjected to treatment, the steam of the mixture of the compressed air and the abrasive substances traveling through the delivery hole is caused to strike the surface portion of the human tissue facing the delivery hole, wherein after striking the surface portion of the human tissue, a mixture of the compressed air and used abrasive substances containing the abrasive substances and tissues removed from the surface portion is collected in the collection reservoir via the output opening of the peeling tool and the used abrasive substance inlet member of the collection reservoir, wherein the air filtering outlet member of the collection reservoir filters the used substances and stores in the collection reservoir while sucking the compressed air by the suction pump via the first air duct; and a purging arrangement comprising a first switch means, which comprises a control switch valve connected at the first air dust, for regulating the compressed air flowing from the air filtering outlet member of the collection reservoir to the suction pump normally, and being selectively switched to cut off the connection between collection reservoir and the air inlet of the suction pump while instantaneously connecting the air outlet of the suction pump to the air filtering outlet member instead, so as to deliver the air output from the air outlet of the suction pump reversely to the air filtering outlet member for purging a clogged condition thereof, and a second switch means for normally ensuring the air outlet of the suction pump connected to outside and selectively switching to instantaneously connect the air outlet of the suction pump to the fresh substance outlet member of the abrasive substance supply means so as to deliver the air output from the air outlet of the suction pump reversely to the fresh substance outlet member for purging a clogged condition thereof

DETAILED DESCRIPTION OF THE PREFERRED EMBODIMENT

Figure 1:
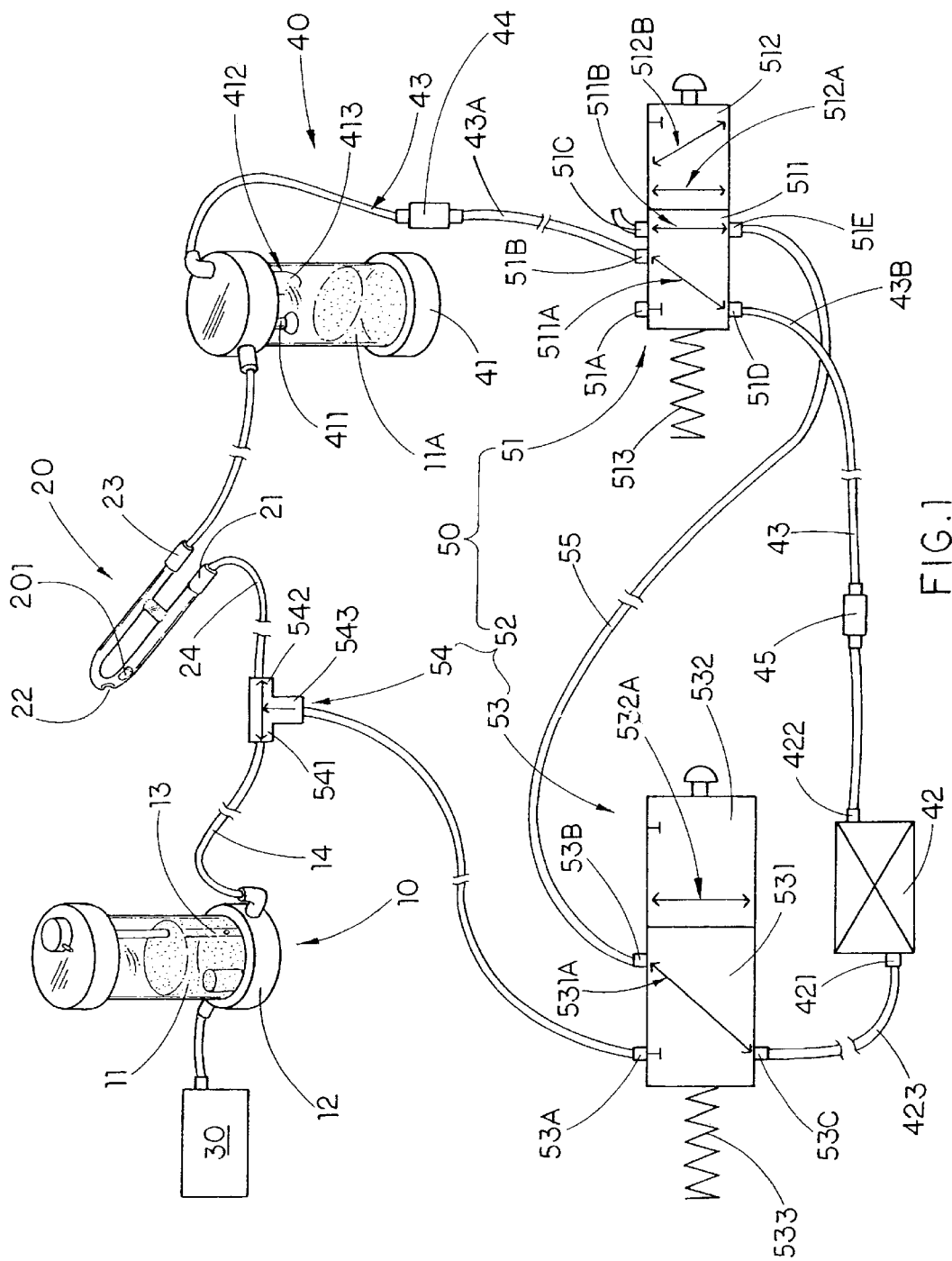
FIG. 1 is a schematic view of a peeling apparatus for removing surface portions of human tissue with a purging arrangement according to a preferred embodiment of the present invention.
Figure 2:
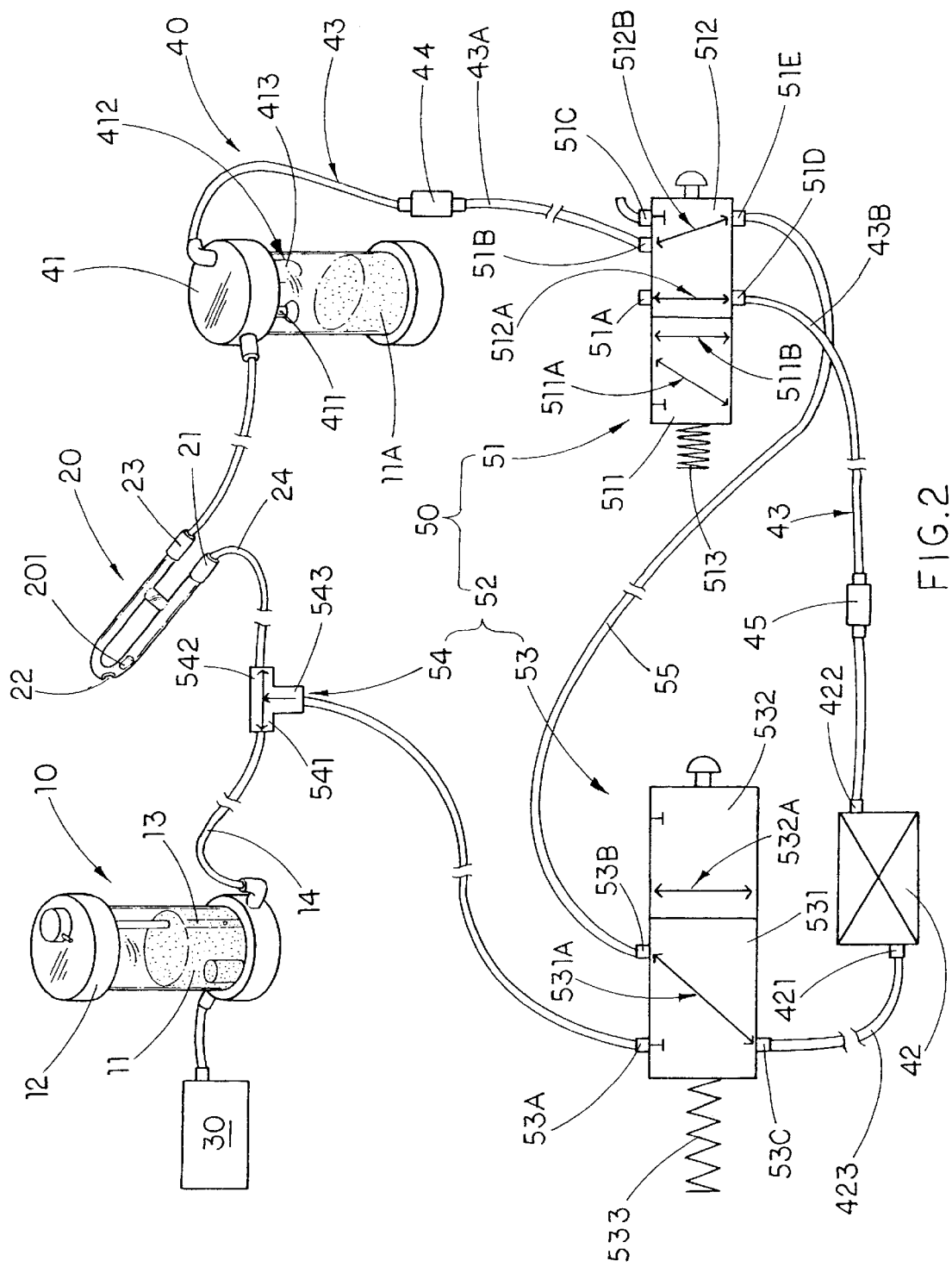
FIG. 2 is a schematic view of the peel apparatus as shown in FIG. 1 wherein the purging arrangement is functioned to purge the clogged condition of the air filtering outlet member of the collection reservoir.
Figure 3:
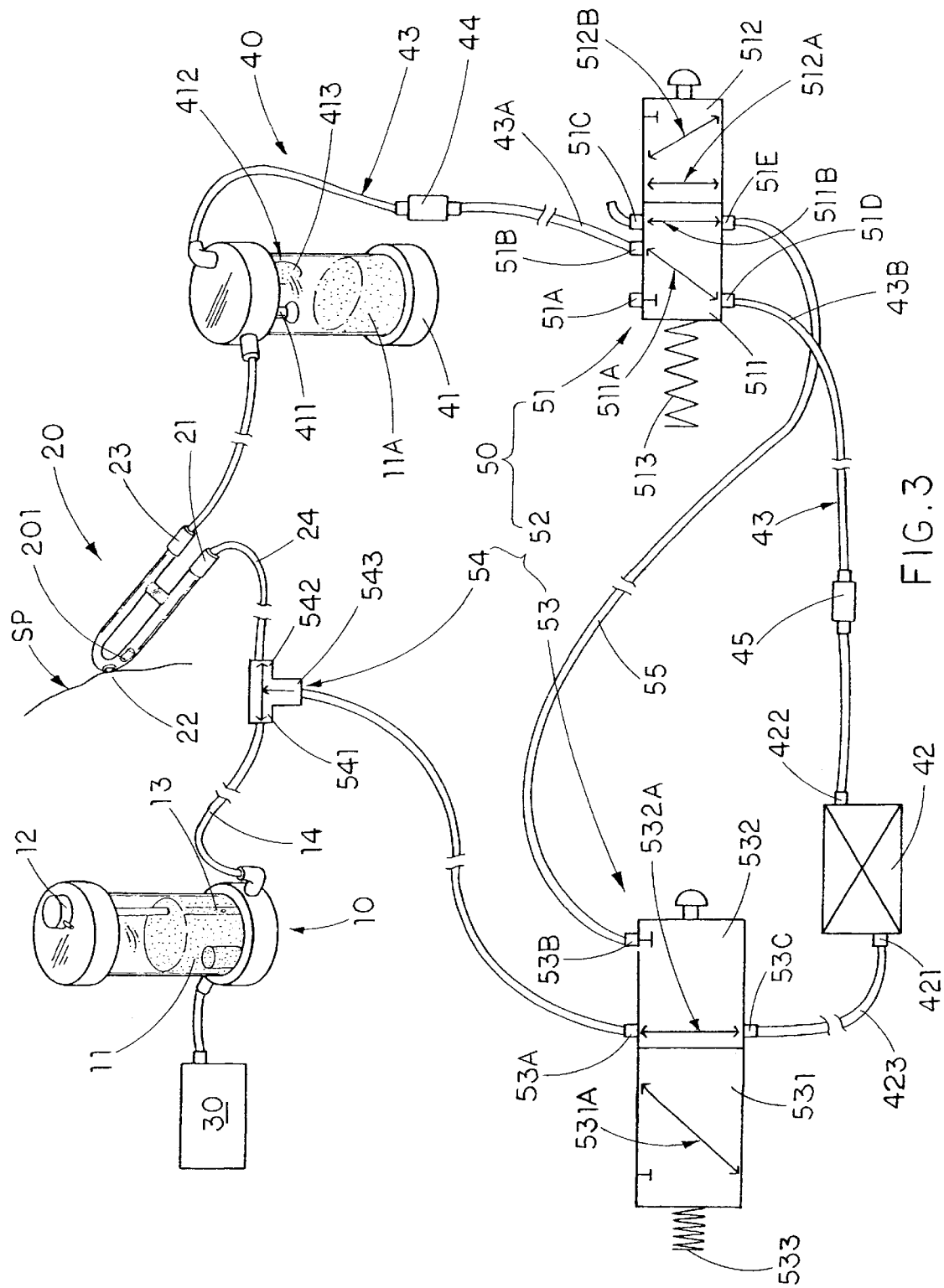
FIG. 3 is a schematic view of the peel apparatus as shown in FIG. 1 wherein the purging arrangement is functioned to purge the clogged condition of the fresh substance outlet member of the abrasive substance supply means.

Referring to FIGS. 1 to 3, a peeling apparatus for removing surface portions of human tissue according to a preferred embodiment of the present invention is illustrated. The peeling apparatus is adapted for removing surface portions of human tissue by superficial abrasion caused by a stream of a mixture of air with at least one granular abrasive substance striking on the surface portion of the human tissue to be removed, wherein the peeling apparatus comprises an abrasive substance supply means 10, a peeling tool 20, a pressurized fluid generating means 30, a suction means 40, and a purging arrangement 50.

The abrasive substance supply means 10 is adapted for supplying granular abrasive substances 11, such as microcrystals of quartz, metal, dust, or derivatives of aluminum, which comprises a supply reservoir 12 storing a predetermined amount of the fresh abrasive substance 11 therein and a fresh substance outlet member 13 having one end extended to disposed at a bottom portion inside the supply reservoir.

The peeling tool 20, which is an instrument adapted to be manipulated by a medical operator to remove the surface portions of the human tissue, has an input opening 21, a delivery hole 22 and an output opening 23, wherein the input opening 21 is connected to the fresh substance outlet member 13 of the supply reservoir 12.

The pressurized fluid generating means 30, such as a compressor, for generating compressed air delivering to the abrasive substance supply means 10 so as to maintain under pressure air within the supply reservoir 12 so as to provide a stream of compressed air to mix with the granular abrasive substance 11 to enhance the delivering the abrasive substances 11 from the fresh substance outlet member 13 to the peeling tool 20 through the input opening 21 thereof.

The suction means 40 is adapted for providing a negative air pressure environment within the supply reservoir so as to cause a stream of a mixture of air and the granular abrasive substance traveling from the fresh substance outlet member to the peeling tool through the input opening thereof.

The suction means comprises a collection reservoir 41 having a used substance inlet member 411 connected to the output opening 23 of the peeling tool 20 and an air filtering outlet member 412, and a suction pump 42 having an air outlet 421 and an air inlet 422 connecting with the air filtering outlet member 412 of the collection reservoir 41 through a first air duct 43.

The suction means 40 may further comprises a first filter 44 and a second filter 45 connected at the first air duct 43 near the air filtering outlet member 412 and the air inlet 422 of the section pump 42 so as to further prevent any abrasive substance entering the section pump 42.

It is worth to mention that since the filtering function provided by the air filtering outlet member 412 is mainly relied on a filter head 413 extended into the collection reservoir 41, when moisture and crystal quality produce a clog at such a filter head 413 made of dense foaming material, the entire system will quickly shut down.

By keeping in contact the delivery hole 22 with the surface portion SP of the human tissue to be subjected to treatment, as shown in FIG. 3, the steam of the mixture of the compressed air and the abrasive substances 11 traveling through the delivery hole 22 is caused to strike the surface portion SP of the human tissue facing the delivery hole 22.

After striking the surface portion SP of the human tissue, a mixture of the compressed air and used abrasive substances 11A containing the abrasive substances 11 and tissues removed from the surface portion is collected in the collection reservoir 41 via the output opening 23 of the peeling tool 20 and the used substance inlet member 411 of the collection reservoir 41, wherein the air filtering outlet member 412 of the collection reservoir 41 filters the used abrasive substances 11A and stores in the collection reservoir 41 while sucking the compressed air by the suction pump 42 via the first air duct 43.

The purging arrangement 50 comprises a first switch means 51 and a second switch means 52.

The first switch means 51, connecting at the first air dust 43, for regulating the compressed air flowing from the air filtering outlet member 412 of the collection reservoir 41 to the suction pump 42 normally, and being selectively switched to cut off the connection between collection reservoir 41 and the air inlet 422 of the suction pump 42 while instantaneously connecting the air outlet 421 of the suction pump 42 to the air filtering outlet member 412 instead, so as to deliver the air output from the air outlet 421 of the suction pump 42 reversely to the air filtering outlet member 412 for purging a clogged condition thereof.

The second switch means 52 for normally ensuring the air outlet 421 of the suction pump 42 connected to outside and selectively switching to instantaneously connect the air outlet 421 of the suction pump 42 to the fresh substance outlet member 13 of the abrasive substance supply means 10 so as to deliver the air output from the air outlet 421 of the suction pump 42 reversely to the fresh substance outlet member 13 for purging a clogged condition thereof.

According to the preferred embodiment of the present invention as illustrated in FIGS. 1 to 3, the first switch means 51 comprises a first control switch valve which includes a first normal section 511, a first purge section 512, and a first resilient means 513 for normally maintaining the collection reservoir 41 is communicated with the section pump 42 via the first normal section 511 which provides a first passage 511A connect a first section 43A of the first air duct 43 extended from the air filtering outlet member 412 with a second section 43B of the first air duct 43 extended from the air inlet 422 of the suction pump 42. The first normal section 511 further provides a second passage 511B connecting to atmosphere.

Moreover, the second switch means 52 comprises a second control switch valve 53 which includes a second normal section 531, a second purge section 532, and a second resilient means 533 for normally maintaining the air output 421 of the section pump 42 is communicated with the first normal section 511 of the first switch means 52 via the second normal section 531. The second normal section 531 provides a normal passage 531A to connect the air outlet 421 of the section pump 42 with the second passage 511B of the first normal section 511 of the control switch valve 51, so as to exhaust the air from the air outlet 421 of the suction pump 42 to the atmosphere via the second control switch valve 53 and the first control switch valve 51, as shown in FIG. 1.

The first purge section 512 of the first control switch valve 51 comprises a first purge passage 512A and a second purge passage 512B. Also, the second purge section 532 of the second control switch valve 53 comprises a purge passage 532A.

The second switch means 52 further comprises a flow valve 54, which is a single way three-end valve only enabling air flowing from the suction pump 42 to the supply reservoir 12 and the peeling tool 20 but blocking any air flowing in reverse direction to the section pump 42.

The flow valve 54 has a first end 541 connected to the fresh substance outlet member 13 of the abrasive substance supply means 10 via a first connecting tube 14, a second end 542 connected to the input opening 21 of the peeling tool 20 via a second connecting tube 24, and a third end 543 connected to a first output terminal 53A provided at a first end of the second control switch valve 53.

The second control switch valve 53 further has a second output terminal 53B provided at the first end of the second control switch valve 53 and an input terminal 53C provided at a second end of the second control switch valve 53 for connecting with the air outlet 421 of the section pump 42 via a second air duct 423.

According to the preferred embodiment, the first control switch valve 51 further has a first, a second and a third air terminal 51A, 51B and 51C provided at a first end thereof, and a fourth and a fifth air terminal 51D, 51E provided at a second end thereof The first air terminal 51A and the third air terminal 51C are connected to the atmosphere. The second air terminal 51B connected to the air filtering outlet member 412 via the first section 43A of the first air duct 43. The fourth air terminal 51D is connected to the air inlet 422 of the section pump 42 via the second section 43B of the first air duct 43. The fifth air terminal 51E is connected with the second input terminal 53B of the second control switch valve 53 via a third air duct 55.

As shown in FIG. 1, normally, the first normal section 511 of the first control switch valve 51 is maintained by the resilient means 513 to position between the first, second and third air terminals 51A, 51B, 51C and the fourth and fifth air terminals 51D. 51E, wherein the first air terminal 51A is blocked, the second air terminal 51B is connected with the fourth air terminal 51D via the first passage 511A, and the third air terminal 51C that is extended to the atmosphere is connected with the fifth air terminal 51E via the second passage 511B. Therefore, the peeling apparatus as shown in FIG. 1 is normally functioned, where the filtered air output from the air filtering outlet member 412 of the collection reservoir 41 will be sucked by the section pump 42 to flow through the first passage 511A of the first normal section 511 into air inlet 422 of the section pump 42. The air exhausted from the air outlet 421 of the suction pump 42 is delivered to the atmosphere via the second air duct 423, the normal passage 531A, the third air duct 55, and the second passage 511B.

However, as shown in FIG. 2, when the air filtering outlet member 412 is clogged, the entire system will shut down. By means of the purging arrangement 50 of the present invention, the operator can release the clogged condition and put the apparatus in normal function again by pushing and maintaining the first control switch valve 51 to a purging position where the second purge section 512 thereof is positioned between the first, second and third air terminals 51A, 51B, 51C at one end of the first control switch valve 51 and the fourth and fifth air terminals 51D, 51E at another end of the first control switch valve 51. At this purging position, the first air terminal 51A is connected with the fourth air terminal 51D via the first purge passage 512A so as to connect the air inlet 422 of the section pump 42 with the atmosphere. The third air terminal 51C is blocked. The second air terminal 51B is connected to the fifth air terminal 51E via the second purge passage 512B so as to deliver the exhaust air from the air outlet 421 of the suction pump 42 to the air filtering outlet member 412 of the collection reservoir 42. Therefore, the reverse flow of the exhaust air from the suction pump 42 will blow off the used abrasive substances 11A clogged thereon back in the collection reservoir 41 and purge the air filtering outlet member 412 for normal functioning again.

Practically, the operator has to switch the first control switch valve 51 to the purging position as shown in FIG. 2 for one to two seconds, thereafter the resilient means 513 will rebound the first control switch valve 51 to return to its normal condition as shown in FIG. 1 automatically when the pushing force of the operator is released.

As shown in FIG. 3, the moisture and quality of the abrasive substances 11 will also produce clog condition at the fresh substance outlet member 13 and even an emit nozzle 201 provided adjacent the delivery hole 22 of the peeling tool 20. By means of the purging arrangement 50 of the present invention, the operator can release such clogged condition and put the apparatus in normal function again by pushing and maintaining the second control switch valve 52 to a purging position where the second purge section 532 thereof is positioned between the first and second output terminals 53A, 53B at one end of the second control switch valve 52 and the input terminal 53C at another end of the second control switch valve 52. At this purging position, the second output terminal 53B is blocked and the first output terminal 53A is connected with the input terminal 53C via the purge passage 532A so as to connect the air inlet 422 of the section pump 42 to the flow valve 54. So that the exhaust air from the air outlet 421 of the suction pump 42 is delivered to the fresh substance outlet member 13 and even the emit nozzle 201 of the peeling tool 20, so as to provide a reverse flow of the exhaust air from the suction pump 42 to blow off the abrasive substances 11 clogged at the nozzle 201 and the fresh substance outlet member 13 back in the supply reservoir 12.

Practically, the operator has to switch the second control switch valve 52 to the purging position as shown in FIG. 3 for one to two seconds, thereafter the resilient means 523 will rebound the second control switch valve 52 to return to its normal condition as shown in FIG. 1 automatically when the pushing force of the operator is released.

What is claimed is:

1. A peeling apparatus for removing a surface portion of a human tissue by abrasion caused by a stream of a mixture of air with at least one granular abrasive substance striking on said surface portion of said human tissue to be removed, wherein said peeling apparatus comprises:

an abrasive substance supply means supplying granular abrasive substances, which comprises a supply reservoir storing a predetermined amount of fresh abrasive substance therein, and a fresh substance outlet member extended into said supply reservoir;

a peeling tool, which is an instrument adapted to be manipulated to remove said surface portion of said human tissue, having an input opening, a delivery hole and an output opening, wherein said input opening is connected to said fresh substance outlet member of said supply reservoir;

a suction means for providing a negative air pressure environment within said supply reservoir so as to cause a stream of a mixture of air and said granular abrasive substance traveling from said fresh substance outlet member to said peeling tool through said input opening thereof, said suction means comprising a collection reservoir having a used substance inlet member connected to said output opening of said peeling tool and an air filtering outlet member, and a suction pump having an air outlet and an air inlet connecting with said air filtering outlet member of said collection reservoir through a first air duct, wherein by keeping in contact said delivery hole with said surface portion of said human tissue to be subjected to treatment, said steam of said mixture of said air and said abrasive substances traveling through said delivery hole is caused to strike said surface portion of said human tissue facing said delivery hole, wherein after striking said surface portion of said human tissue, a mixture of said air and used abrasive substances containing said abrasive substances and tissues removed from said surface portion is collected in said collection reservoir via said output opening of said peeling tool and said used abrasive substance inlet member of said collection reservoir, wherein said air filtering outlet member of said collection reservoir filters said used substances and stores in said collection reservoir while sucking said air by said suction pump via said first air duct; and a purging arrangement, comprising a first switch means, which comprises a control switch valve connected at said first air dust, for regulating said compressed air flowing from said air filtering outlet member of said collection reservoir to said suction pump normally, and being selectively switched to cut off said connection between collection reservoir and said air inlet of said suction pump while instantaneously connecting said air outlet of said suction pump to said air filtering outlet member instead, so as to deliver said air output from said air outlet of said suction pump reversely to said air filtering outlet member for purging a clogged condition thereof; and a second switch means for normally ensuring said air outlet of said suction pump connected to outside and selectively switching to instantaneously connect said air outlet of said suction pump to said fresh substance outlet member of said abrasive substance supply means so as to deliver said air output from said air outlet of said suction pump reversely to said fresh substance outlet member for purging a clogged condition thereof.

2. The peeling apparatus, as recited in claim 1, wherein said control switch valve is a first control switch valve which includes a first normal section, a first purge section, and a first resilient means for normally maintaining said collection reservoir communicated with said suction pump via said first normal section which provides a first passage connect a first section of said first air duct extended from said air filtering outlet member with a second section of said first air duct extended from said air inlet of said suction pump, and that said first normal section further provides a second passage connecting to atmosphere.

3. The peeling apparatus, as recited in claim 2, wherein said second switch means comprises a second control switch valve which includes a second normal section, a second purge section, and a second resilient means for normally maintaining said air output of said suction pump communicated with said first normal section of said first switch means via said second normal section, wherein said second normal section provides a normal passage to connect said air outlet of said suction pump with said second passage of said first normal section of said first control switch valve, so as to exhaust said air from said air outlet of said suction pump to said atmosphere via said second control switch valve and said first control switch valve.

4. The peeling apparatus, as recited in claim 3, wherein said second switch means further comprises a flow valve, which is a single way three-end valve only enabling air flowing from said suction pump to said supply reservoir and said peeling tool but blocking any air flowing in reverse direction to said section pump.

5. The peeling apparatus, as recited in claim 3, wherein said first purge section of said first control switch valve comprises a first purge passage and a second purge passage, and that said second purge section of said second control switch valve comprises a purge passage.

6. The peeling apparatus, as recited in claim 4, wherein said second switch means further comprises a flow valve, which is a single way three-end valve only enabling air flowing from said suction pump to said supply reservoir and said peeling tool but blocking any air flowing in reverse direction to said suction pump.

7. The peeling apparatus, as recited in claim 6, wherein said first control switch valve further has a first, a second and a third air terminal provided at a first end thereof, and a fourth and a fifth air terminal provided at a second end thereof, said first air terminal and said third air terminal being connected to said atmosphere, said second air terminal being connected to said air filtering outlet member via said first section of said first air duct, said fourth air terminal being connected to said air inlet of said suction pump via said second section of said first air duct, said fifth air terminal being connected with said second input terminal of said second control switch valve via a third air duct.

8. The peeling apparatus, as recited in claim 7, wherein said first normal section of said first control switch valve is maintained by said resilient means to position between said first, second and third air terminals and said fourth and fifth air terminals, wherein said first air terminal is blocked, said second air terminal is connected with said fourth air terminal via said first passage, and said third air terminal that is extended to said atmosphere is connected with said fifth air terminal via said second passage, therefore when said peeling apparatus is normally functioned, said filtered air output from said air filtering outlet member of said collection reservoir is sucked by said suction pump to flow through said first passage of said first normal section into said air inlet of said suction pump, and said air exhausted from said air outlet of said suction pump is delivered to said atmosphere via said second air duct, said normal passage, said third air duct, and said second passage;

whereby by switching said first control switch valve to a purging position where said second purge section thereof is positioned between said first, second and third air terminals and said fourth and fifth air terminals, said first air terminal is connected with said fourth air terminal via said first purge passage so as to connect said air inlet of said suction pump with said atmosphere, wherein said third air terminal is blocked and said second air terminal is connected to said fifth air terminal via said second purge passage so as to deliver said exhaust air from said air outlet of said suction pump to said air filtering outlet member of said collection reservoir, therefore said exhaust air reversely flows from said suction pump to blow off said used abrasive substances clogged thereon back in said collection reservoir and purge said air filtering outlet member for normal functioning again;

moreover by switching said second control switch Valve to a purging position where said second purge section thereof is positioned between said first and second output terminals and said input terminal, wherein said second output terminal is blocked and said first output terminal is connected with said input terminal via said purge passage 532A so as to connect said air inlet of said suction pump to said flow valve, so that said exhaust air from said air outlet of said suction pump is delivered to said fresh substance outlet member, so as to provide a reverse flow of said exhaust air from said suction pump 42 to blow off said abrasive substances 11 clogged at said nozzle 201 and said fresh substance outlet member 13 back in said supply reservoir 12.

9. The peeling apparatus, as recited in claim 6, wherein said flow valve has a first end connected to said fresh substance outlet member of said abrasive substance supply means via a first connecting tube, a second end connected to said input opening of said peeling tool via a second connecting tube, and a third end connected to a first output terminal provided at a first end of said second control switch valve.

10. The peeling apparatus, as recited in claim 9, wherein said second control switch valve further has a second output terminal provided at said first end of said second control switch valve and an input terminal provided at a second end of said second control switch valve for connecting with said air outlet of said suction pump via a second air duct.

11. The peeling apparatus, as recited in claim 10, wherein said first control switch valve further has a first, a second and a third air terminal provided at a first end thereof, and a fourth and a fifth air terminal provided at a second end thereof, said first air terminal and said third air terminal being connected to said atmosphere, said second air terminal being connected to said air filtering outlet member via said first section of said first air duct, said fourth air terminal being connected to said air inlet of said suction pump via said second section of said first air duct, said fifth air terminal being connected with said second input terminal of said second control switch valve via a third air duct.

12. The peeling apparatus, as recited in claim 11, wherein said first normal section of said first control switch valve is maintained by said resilient means to position between said first, second and third air terminals and said fourth and fifth air terminals, wherein said first air terminal is blocked, said second air terminal is connected with said fourth air terminal via said first passage, and said third air terminal that is extended to said atmosphere is connected with said fifth air terminal via said second passage, therefore when said peeling apparatus is normally functioned, said filtered air output from said air filtering outlet member of said collection reservoir is sucked by said suction pump to flow through said first passage of said first normal section into said air inlet of said suction pump, and said air exhausted from said air outlet of said suction pump is delivered to said atmosphere via said second air duct, said normal passage, said third air duct, and said second passage;

whereby by switching said first control switch valve to a purging position where said second purge section thereof is positioned between said first, second and third air terminals and said fourth and fifth air terminals, said first air terminal is connected with said fourth air terminal via said first purge passage so as to connect said air inlet of said suction pump with said atmosphere, wherein said third air terminal is blocked and said second air terminal is connected to said fifth air terminal via said second purge passage so as to deliver said exhaust air from said air outlet of said suction pump to said air filtering outlet member of said collection reservoir, therefore said exhaust air reversely flows from said suction pump to blow off said used abrasive substances clogged thereon back in said collection reservoir and purge said air filtering outlet member for normal functioning again.

\* \* \* \* \*